United States Patent [19]

Krygier

[11] 4,144,643

[45] Mar. 20, 1979

[54] MAXILLARY ORTHOPEDIC SUTURE SEPARATING ORTHODONTIC APPLIANCE

[76] Inventor: Stanley J. Krygier, Suite 103 Plaza Apt. Bldg., 1303 Delaware Ave., Wilmington, Del. 19806

[21] Appl. No.: 760,444

[22] Filed: Jan. 19, 1977

[51] Int. Cl.² ............................................... A61C 7/00
[52] U.S. Cl. .................................................... 32/14 E
[58] Field of Search .................. 32/14 E, 14 R, 14 A; 254/67, 100

[56] References Cited

U.S. PATENT DOCUMENTS

| | | | |
|---|---|---|---|
| 360,695 | 4/1887 | Holmes | 32/14 E |
| 934,958 | 9/1909 | Case | 32/14 E |
| 986,076 | 3/1911 | Montag | 32/14 A |
| 1,014,030 | 1/1912 | Angle | 32/14 A |
| 3,454,001 | 7/1969 | Stockfish | 32/14 A |
| 3,835,540 | 9/1974 | Biederman | 32/14 E |
| 3,977,082 | 8/1976 | Siatkowski | 32/14 E |

FOREIGN PATENT DOCUMENTS

| | | | |
|---|---|---|---|
| 352360 | 4/1921 | Fed. Rep. of Germany | 32/14 E |
| 668227 | 3/1952 | United Kingdom | 32/14 E |

*Primary Examiner*—Russell R. Kinsey
*Assistant Examiner*—John J. Wilson
*Attorney, Agent, or Firm*—Connolly and Hutz

[57] ABSTRACT

A maxillary orthopedic suture separating orthodontic appliance includes a pair of spaced anchor plates which are secured to bands on the teeth at opposite sides of the upper jaw and are connected together by offset adjusting means disposed for fitting in the palatal area.

10 Claims, 7 Drawing Figures

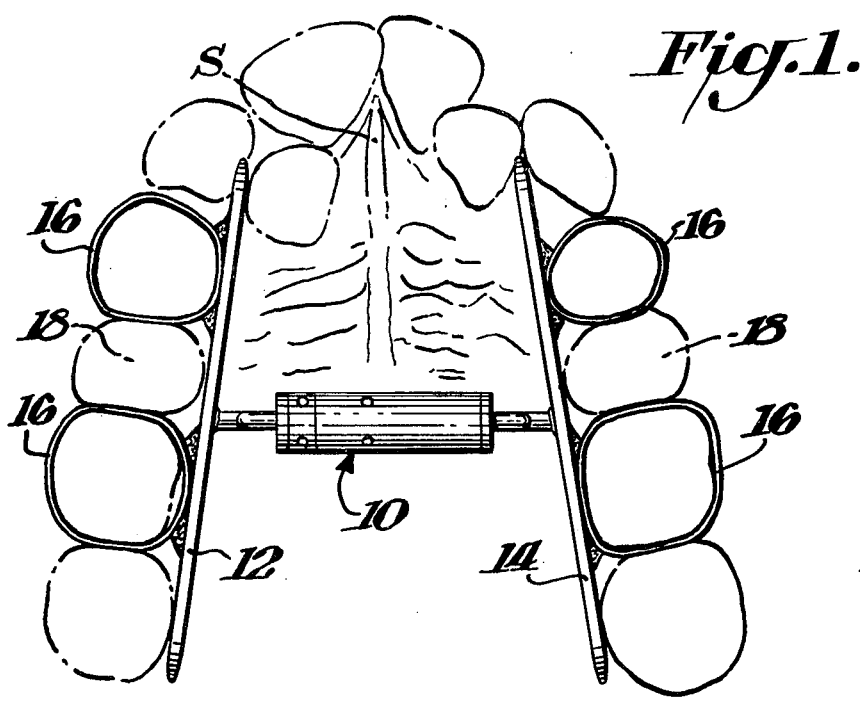
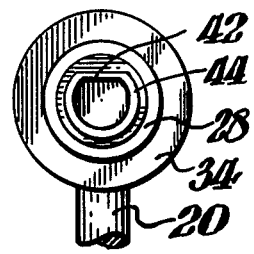
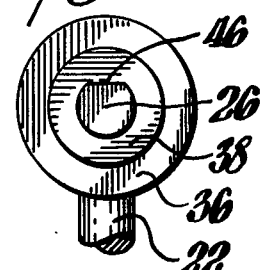
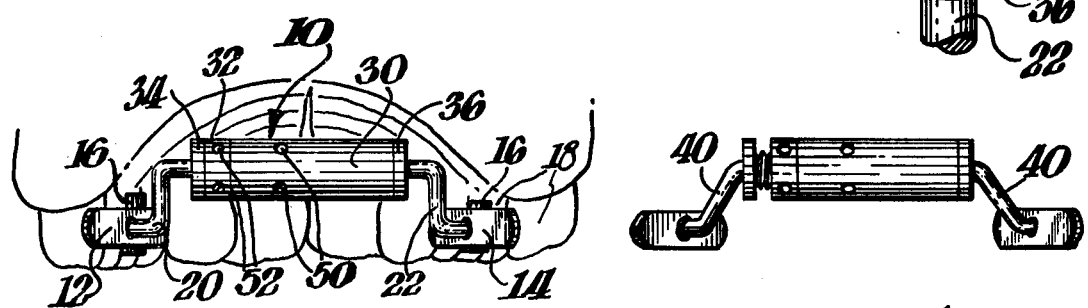
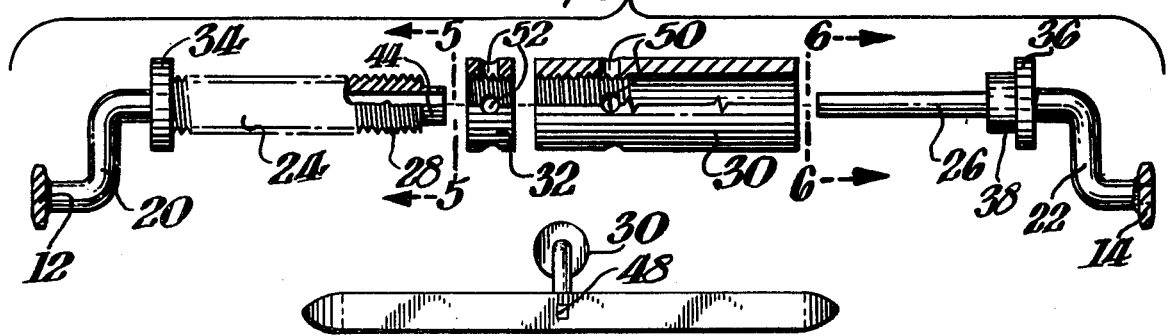

MAXILLARY ORTHOPEDIC SUTURE SEPARATING ORTHODONTIC APPLIANCE

BACKGROUND OF THE INVENTION

Various orthodontic appliances exist for various purposes. One such appliance is an expander used on the upper jaw wherein plates on opposite sides of the jaw are expanded or forced apart. A drawback with conventional maxillary orthopedic suture separating appliances is that the plates on such appliances are connected by adjusting members which extend thereacross in the same plane thereof. This has the disadvantage of interferring with the tongue and otherwise being uncomfortable to the user.

SUMMARY OF THE INVENTION

An object of this invention is to provide an orthopedic orthodontic appliance which will separate the maxillary suture thereby moving both sides of the maxillary palatal bones sideways. As this gentle pressure is exerted the sutural space is filled in with hard cortical bone.

A further object of this invention is to provide such an appliance which may be precisely adjusted in a quick and convenient manner.

In accordance with this invention a maxillary orthopedic suture separating orthodontic appliance or expander includes a pair of spaced anchor plates which are secured to bands on the teeth at opposite sides of the upper jaw and are connected together by offset adjusting means disposed for fitting in the palatal area. the adjusting means preferably comprises an internally threaded barrel or sleeve engaged with an externally threaded rod secured to one of the anchor plates while a non-threaded or smooth rod secured to the other anchor plate is telescopically arranged in the threaded rod. The smooth rod includes an abutment for contacting the threaded sleeve. In this manner the sleeve can be manipulated on the threaded rod to thereby control the extent of telescoping of the smooth rod into the threaded rod for precisely controlling the spacing between the anchor plates.

THE DRAWINGS

FIG. 1 is a bottom plan view of an orthodontic appliance or expander in accordance with this invention;

FIG. 2 is a front elevation view of the orthodontic appliance shown in FIG. 1;

FIG. 3 is a front elevation view of the orthodontic appliance shown in FIGS. 1-2;

FIG. 4 is an exploded view in elevation partly in section of the orthodontic appliance shown in FIGS. 1-3;

FIG. 5 is an end elevation view of the orthodontic appliance as viewed from the line 5—5 of FIG. 4;

FIG. 6 is an end elevation view of the orthodontic appliance as viewed from the line 6—6 of FIG. 4; and FIG. 7 is a front elevation view similar to FIG. 2 showing a modified form of orthodontic appliance in a different phase of adjustment in accordance with this invention.

DETAILED DESCRIPTION

FIG. 1 is a bottom plan view of a maxillary orthopedic suture separating orthodontic appliance 10 in accordance with this invention. As indicated therein, appliance 10 includes a pair of spaced flat plates 12, 14 which are secured in any suitable manner as by soldering to a pair of bands 16 on each side of the upper jaw. Although FIG. 1 illustrates each plate 12, 14 secured to a pair of such bands the invention may also be practiced by securing each plate 12, 14 to only a single band located around the second premolars (bicuspids) teeth 18 on each side of a jaw whereby only a single band (not shown) would be utilized as means of securement.

FIG. 4 illustrates the various components which comprise appliance or expander 10. As indicated therein, each of plate 12 and plate 14 is secured to a connecting member 20, 22 secured at the end of a rod 24, 26, respectively. Rod 24 is of hollow tube-like construction as later described and has a threaded outer surface 28. Rod 26, however, has a smooth outer surface and preferably is solid. An internally threaded barrel or sleeve 30 and an internally threaded lock nut 32 also form part of appliance 10. In practice rod 26 is loosely telescoped into the hollow interior of rod 24 while lock nut 32 and sleeve 30 are threadably engaged on threaded outer surface 28. Threaded rod 24 includes a circular flange stop shoulder 34 disposed for contacting lock nut 32, while smooth rod 26 likewise includes a circular flange stop shoulder 36 for contacting sleeve 30. Smooth rod 26 is also provided with a boss 38 for fitting within sleeve 30. Stop shoulders 34 and 36 have the same outer configuration as lock nut 32 and sleeve 30 so that in its completely closed condition (as illustrated in FIG. 2) these various components appear to form a single continuous smooth outer surface thus minimizing any possibility of collecting food, etc., or otherwise interferring with the tongue. It is to be understood of course that any other geometric shape may be used for these various components with or without the resultant formation of the preferred single smooth continuous type of formation.

Connecting members 20 and 22 are generally S-shaped so that the adjusting means which is comprised of rods 24 and 26, sleeve 30 and lock nut 32 is displaced above anchor plates 12, 14 generally in and confirming to the palatal area. It is to be understood that other types of connecting members may be used to accomplish the same general results. For example, FIG. 7 illustrates connecting members 40 which are inclined from the anchor plates generally directly to the rods rather than having the vertical intermediate sections of the S-shaped connecting members 20, 22.

Since the adjusting means is upwardly displaced from anchor plates 12, 14 it is essential that the various components of appliance 10 be maintained in their proper orientation. This invention makes provisions for such maintenance of orientation. For example as best shown in FIG. 5 threaded rod 24 is of tube-like hollow construction having at its upper edge a flattened portion 42. Such flattened portion 42 may be conveniently achieved by simply crimping the upper portion of smooth extension 44 which is outwardly beyond the threaded surface 28 (FIG. 4). Smooth rod 26 likewise has a complementary outer surface which includes a flattened upper portion 46 as shown in FIG. 6 to minimize any tendency of smooth rod 26 rotating in threaded rod 24. It is not absolutely critical that all rotation be prevented. What is necessary is that smooth rod 26 should not be permitted to freely rotate completely around within threaded rod 24 and thus rod 26 may be somewhat loosely disposed in rod 24. The complementary shapes of rods 24 and 26, however, assure that anchor plates 12 and 14 will thus be maintained in generally the same plane.

FIG. 3 illustrates further provisions for maintaining the proper orientation between anchor plates 12 and 14. As indicated therein each anchor plate includes a non-circular opening such as the square opening 48 into which is fitted a complementary shaped tip at the end of connector 20 or 22, as the case may be, to thereby assure proper orientation of the connecting member with the anchor plate when these members are later permanently secured as by soldering.

In operation a suitable appliance 10 is selected for a particular patient. Should it be determined that anchor plates 12, 14 are too long, the plates may be cut to the proper size. Similarly a sleeve or barrel 30 is selected of a length appropriate for that patient's needs. Lock nut 32 is screwed onto threaded rod 24 until it is juxtaposed stop member 34. The appropriate sleeve 30 is then threadably engaged with threaded rod 24 until it contacts lock nut 32. Smooth rod 26 is then telescoped into threaded rod 24 until stop shoulder 36 contacts sleeve 30. Appliance 10 is then inserted in the mouth of the patient after soldering to the band. As best shown in FIG. 1, plates 12, 14 converge toward each other generally assuming the inclination of the molars and canine teeth in the upper jaw. During the course of treatment adjustment would be required for spreading the plates apart on each side of the maxillary suture S (FIG. 1). Such adjustment might also be required when the appliance is first mounted in the mouth at the beginning of treatment. This adjustment is accomplished by utilizing a suitable tool such as a wire key which engages in spaced openings 50 in the outer surface of sleeve 30 whereby the sleeve may be rotated outwardly on a threaded rod 24 without requiring the removal of the appliance from the mouth. As sleeve 30 moves outwardly sleeve 30, by its contacting stop shoulder 36, forces anchor plate 14 to likewise move outwardly thereby changing the spacing between plates 12 and 14. In order to maintain this positioning and to thus prevent any inadvertent manipulation of sleeve 30 by, for example, the patient's tongue, lock nut 32 is also moved by engagement with a suitable tool such as a wire key engaged in holes 52 until lock nut 32 contacts sleeve 30 as illustrated in FIG. 7. During the course of treatment when further adjustment is necessary the same manipulations take place.

It should be understood that appliance 10 is particularly advantageous not only for the reasons given above but also because it lends itself to the use of interchangeable parts. Thus, for example, an appropriately sized appliance sleeve or barrel may be utilized with the same basic components in the assembly in accordance with the requirements of different patients.

The appliance of this invention is highly effective for accomplishing a plurality of results. For example, the appliance not only functions orthodontically to move teeth individually, but also functions orthopedically to separate the right and left maxillary bones thereby also moving the teeth sideways en masse. This type of sideways movement is of a more permanent nature minimizing the chances of relapse.

What is claimed is:

1. A maxillary orthopedic suture separating orthodontic appliance comprising a pair of spaced anchor plates for securement to bands on teeth on opposite sides of the upper jaw, adjusting means secured to said plates for linearly moving said plates toward and away from each other in controlled increments, said adjusting means including threaded means which are adjusted by relative rotation thereof without rotating said plates, said adjusting means including an internally threaded elongated rigid sleeve open at both ends thereof, an externally threaded rod threadedly engaged to said sleeve, said threaded rod being hollow and open at one end thereof, a nonthreaded rod telescopically engaging said threaded rod by being inserted therein through said open end of said threaded rod and projecting outwardly therefrom, said sleeve extending longitudinally around both said threaded rod and said non-threaded rod by means of said non-threaded rod being telescoped into said threaded rod and said threaded rod being inserted into said sleeve, an abutment on said non-threaded rod for contacting said sleeve at one of its ends thereof whereby the relative positioning of said sleeve on said threaded rod determines the extent of outward projection of said non-threaded rod from said threaded rod, one of said plates being secured to said non-threaded rod, the other of said plates being secured to said threaded rod whereby the spacing of said plates from each other is determined by the extent of outward projection of said non-threaded rod from said threaded rod, a lock nut threadably engaged on said threaded rod for contacting the other of said ends of said sleeve for fixing said sleeve in position after adjustment thereof on said threaded rod, said lock nut and said sleeve abutting each other when said appliance is in its operative position for preventing accidental rotation of said sleeve, said non-threaded rod being loosely inserted in said threaded rod without physical attachment thereto, said threaded rod having an interior thereof of non-circular cross-section, and the outer surface of said non-threaded rod having a cross-section generally complementary to said non-circular cross-section whereby complete relative rotation of said non-threaded rod in said threaded rod is generally minimized.

2. The appliance of claim 1 wherein said abutment on said non-threaded rod is a circular flange, a circular flange abutment on said threaded rod for contacting said lock nut, each of said circular flanges and said lock nut and said sleeve being of circular cross-section having the same diameter, and said sleeve having a length which covers a substantial distance of the distance between said abutments.

3. The appliance of claim 1 wherein tool receiving holes are in the outer surface of each of said sleeve and said lock nut to facilitate the manipulation thereof.

4. The appliance of claim 1 wherein each of said plates has a non-circular opening therein, said plates being secured to said rods by connecting members, and each of said connecting members terminates in a lower extension of non-circular shape which fits in its respective opening to properly orient its respective rod with its respective plate.

5. The appliance of claim 4 wherein each of said connecting members has an upper extension secured to its rod with an intermediate section secured to its upper extension and its said lower extension, and said abutment on said non-threaded rod having a cylindrical shoulder fitting in said sleeve.

6. The appliance of claim 5 wherein said intermediate section is vertical.

7. The appliance of claim 5 wherein said intermediate section is inclined.

8. The appliance of claim 1, in combination therewith, a first band for securement to a tooth on one side of the jaw and a second band for securement to a tooth on the opposite side of the jaw generally adjacent the point of securement of each of said plates with said adjusting means, said plates converging toward each other from front to rear with respect to the jaw, each of said plates being secured to one of said bands, and said first and said second bands comprising the sole means of securing said appliance to the teeth.

9. The appliance of claim 1 including a connecting member secured at one end thereof to each of said plates and extending upwardly and inwardly therefrom, and said connecting members being secured at their opposite ends thereof to said adjusting means to vertically displace said adjusting means above said plates for disposition in the palatal area.

10. The appliance of claim 1 wherein said non-circular cross-section comprises a generally circular cross-section having a flattened portion thereof.

* * * * *